ns Patent [19]
Bock

[11] Patent Number: 5,162,280
[45] Date of Patent: Nov. 10, 1992

[54] AQUEOUS DISPERSIONS OF AROMATIC DIACYL PEROXIDES

[75] Inventor: Lawrence A. Bock, Walnut Creek, Calif.

[73] Assignee: Witco Corporation, New York, N.Y.

[21] Appl. No.: 780,090

[22] Filed: Oct. 11, 1991

Related U.S. Application Data

[60] Division of Ser. No. 649,171, Feb. 1, 1991, Pat. No. 5,057,479, which is a continuation of Ser. No. 520,860, May 9, 1990, abandoned, which is a continuation of Ser. No. 399,368, Aug. 28, 1989, abandoned, which is a continuation of Ser. No. 149,000, Jan. 27, 1988, abandoned.

[51] Int. Cl.$^5$ .............................................. B01J 31/00
[52] U.S. Cl. ..................................... 502/160; 502/172; 521/69; 521/72; 521/84.1; 521/92; 521/96; 521/138
[58] Field of Search ................... 502/160, 172; 521/69, 521/72, 84.1, 92, 96, 138

[56] References Cited

U.S. PATENT DOCUMENTS

| | | |
|---|---|---|
| 2,343,094 | 2/1944 | Smith . |
| 3,507,800 | 4/1970 | Leveskis . |
| 3,535,422 | 10/1970 | Cox et al. . |
| 3,825,509 | 7/1974 | Miller . |
| 3,988,261 | 10/1976 | Barter et al. . |
| 4,016,112 | 4/1977 | Kajiura et al. . |
| 4,039,475 | 8/1977 | Oosterwijk et al. . |
| 4,056,611 | 11/1977 | Young . |
| 4,092,470 | 5/1978 | Oosterwijk et al. . |
| 4,350,681 | 9/1982 | Fulton, Jr. . |
| 4,355,028 | 10/1982 | Kligman et al. . |
| 4,373,075 | 2/1983 | Schwarz . |
| 4,374,057 | 2/1983 | Goodman et al. . |
| 4,376,719 | 3/1983 | Goodman et al. . |
| 4,377,498 | 3/1983 | Temple . |
| 4,387,107 | 6/1983 | Klein et al. . |
| 4,391,876 | 7/1983 | Tamosauskas et al. . |
| 4,396,527 | 8/1983 | Matsuyama et al. . |
| 4,415,716 | 11/1983 | Lundin et al. . |
| 4,435,473 | 3/1984 | Tamosauskas et al. . |
| 4,439,558 | 3/1984 | Tamosauskas et al. . |
| 4,440,885 | 4/1984 | Tamosauskas et al. . |
| 4,483,784 | 11/1984 | Temple . |
| 4,499,250 | 2/1985 | Lundin et al. . |
| 4,515,928 | 5/1985 | Schwarz . |
| 4,515,929 | 5/1985 | Tang . |
| 4,545,990 | 10/1985 | Le Foyer de Costil et al. . |
| 4,547,481 | 10/1985 | Lundin et al. . |
| 4,552,682 | 11/1985 | Black et al. . |
| 4,563,510 | 1/1986 | Ugelstad . |
| 4,711,909 | 12/1987 | Pastorino et al. ................... 521/138 |

OTHER PUBLICATIONS

"Pumpable peroxide dispersion; a useful new sprayup tool," Modern Plastics, pp. 64-67, Feb. 1984.
Chemical Abstracts report CA 105: 98134f [JP 61 62, 502].
Chemical Abstracts report CA 105: 172053X [JP 61 87,659].

Primary Examiner—Joseph L. Schofer
Assistant Examiner—N. Sarofim
Attorney, Agent, or Firm—Lockwood, Alex, FitzGibbon & Cummings

[57] ABSTRACT

A storage stable aqueous dispersion useful in the curing of unsaturated polyester resins and the suspension polymerization of vinyl monomers containing an aromatic diacyl peroxide, an alkylene glycol and dispersion-stabilizing amounts of magnesium aluminum silicate and a cellulose ether compound is disclosed. Also disclosed are the curing of polyester resins and the suspension polymerization of vinyl monomers using the dispersion.

9 Claims, No Drawings

AQUEOUS DISPERSIONS OF AROMATIC DIACYL PEROXIDES

This application is a divisional of copending application Ser. No. 649,171, filed Feb. 1, 1991 now U.S. Pat. No. 5,057,429, which is a continuation is Ser. No. 520,860, filed May 9, 1990 now abandoned, which was a continuation of Ser. No. 399,368, filed Aug. 28, 1989 now abandoned, which was a continuation of Ser. No. 149,000, filed Jan. 27, 1988 now abandoned.

BACKGROUND OF THE INVENTION

The present invention is generally directed to aqueous dispersions of organic peroxides for use in curing polyester resins and the suspension polymerization of vinyl monomers. More particularly, the present invention is directed to aqueous dispersions of aromatic diacyl peroxides useful as initiators in the curing of unsaturated polyester resins and the suspension polymerization of vinyl monomers such as styrene, vinyl chloride, vinyl alcohol, vinyl acetate, methacrylates and acrylates, etc. In this regard, an important feature of the present invention is the provision of aqueous dispersions of aromatic diacyl peroxides which are pumpable and shelf-stable.

In the curing of polyester resins and the suspension polymerization of vinyl monomers, polymerization initiators are used extensively. Polyester resin compositions generally include mixtures comprising a monomer copolymerizable with an unsaturated organic polymer.

Aromatic diacyl peroxides are well known polymerization initiators. Peroxides have, however, as a general property, a tendency to be flammable and explosive with some peroxides exhibiting such properties to a greater extent than others. For example, benzoyl peroxide may decompose when dry due to shock, friction, or static electricity. This property carries with it the obvious hazards to the users of these materials as well as to the manufacturers and intermediate handlers thereof. One particularly burdensome aspect of this property occurs during shipment of the peroxides. Accordingly, it has long been an object to provide flame resistant organic peroxide compositions. For example, U.S. Pat. No. 3,507,800 is directed to providing a flame resistant peroxide composition consisting essentially of three components—water, peroxide and solvent wherein the water is at least about 18 percent of the composition.

The safety and end-use advantage provided by a water-soluble or a water-emulsifiable initiator is well recognized. In this regard, U.S. Pat. No. 3,825,509 describes a process for the suspension polymerization of vinyl chloride wherein the initiator is an aqueous emulsion of an organic peroxide in which the peroxide is present in an amount up to 19 weight percent. The surfactant used to prepare the aqueous peroxide emulsion is a combination of polyvinyl alcohol and polyoxyethylene sorbitan monolaurate. However, emulsions containing greater than about 19 percent by weight of organic peroxide are described as being too viscous and therefore difficult to handle.

Providing an aqueous emulsion of a highly reactive organic peroxide, in and of itself, is not a guarantee of a safe product, as phase separation can result in a concentrated mass of undiluted organic peroxide. Decomposition of such an undiluted mass of organic peroxide, depending on such things as the total mass, container, temperature of decomposition, etc., can result in a decomposition that is accompanied by the liberation of heat and flammable gases. Such conditions can lead to fires, deflagrations, pressure ruptures and detonations. Further, irrespective of any hazards, phase separation of the initiator emulsion can result in nonuniform concentrations of the initiator being supplied to the polymerization system. Efforts to provide a stable aqueous dispersion of organic peroxide include U.S. Pat. No. 3,988,261 which is directed to frozen aqueous emulsions of organic peroxides having a moderate to high concentration of organic peroxides. It has been suggested that such emulsions can be frozen without separation of the organic peroxide phase and water phase and, when thawed, retain their emulsified state at least for a period of time sufficient to allow safe handling and use. Although the frozen emulsified peroxide compositions of U.S. Pat. No. 3,988,261 may provide advantages for the handling of highly reactive peroxides, it is necessary for the end-user to provide special equipment for handling and thawing the frozen product. Consequently, it would be even more desirable to provide a pumpable product which can be shipped and forwarded directly from on-sight storage to the polymerization vessel.

Various compositions have been proposed for providing stable, pumpable, aqueous suspensions of organic peroxides. For instance, U.S. Pat. No. 4,039,475 discloses a pumpable aqueous suspension of organic peroxide solid at about 20° C. containing a combination of at least 0.2 percent by weight of a non-ionic emulsifier having a maximum HLB-value of 12.5 and at least 0.2 percent by weight of a non-ionic emulsifier with an HLB-value not lower than 12.5 or at least 0.01 percent by weight of an anionic emulsifier as well as a water-soluble cellulose derivative as a thickener.

Another shelf-stable mobile free-radical generating initiator that can be readily pumped into a polymerization reactor and readily dispersed throughout an aqueous polymerization medium was described in U.S. Pat. No. 4,376,719 which discloses forming an aqueous dispersion by adding an initiator, such as benzoyl peroxide, to an aqueous system that contains a water-soluble suspending agent, such as water-soluble cellulose derivatives, and a wetting agent that may be non-ionic or anionic and homogenizing the suspension to form a stable initiator dispersion.

U.S. Pat. No. 4,415,716 proposes yet another composition for providing an aqueous dispersion of a free-radical forming initiator, which dispersion is stable and easy to handle. According to U.S. Pat. No. 4,415,716 such initiator dispersions are provided by an emulsifier system consisting of (a) an ethoxylated non-ionic emulsifier with an HLB-value above 15, which in most part does not contain cyclic inner ether bonds, and (b) a non-ethoxylated non-ionic emulsifier with an HLB-value below 9, whereby the resulting HLB-value of the emulsifier blend is within the range of 11–17.

Despite the numerous disclosures of organic peroxide dispersions useful as polymerization initiators, there is a need for improved aromatic diacyl peroxide dispersions that are stable and permit the initiator to be available in the polymerization mixture for initiating the curing of the unsaturated polyester or the suspension polymerization of vinyl monomers.

Accordingly, it is a general object of the present invention to provide an aqueous dispersion of a free-radical polymerization initiator or catalyst.

Another object of the present invention is to provide an improved aqueous dispersion of an aromatic diacyl peroxide polymerization initiator which dispersion is pumpable and easy to handle.

Another object of the present invention is to provide an aqueous dispersion of an aromatic diacyl peroxide polymerization initiator which is relatively shelf-stable.

Another object of the present invention is to provide a method for stabilizing a pumpable aqueous dispersion of an aromatic diacyl peroxide polymerization initiator useful for curing polyester resins.

Another object of the present invention is to provide a method for stabilizing a pumpable aqueous dispersion of an aromatic diacyl peroxide polymerization initiator useful for the suspension polymerization of vinyl monomers.

Another object of the present invention is to provide a method for curing unsaturated polyester resins.

Another object of the present invention is to provide a method for the suspension polymerization of vinyl monomers.

These and other objects of the present invention will be apparent from the following detailed description thereof.

SUMMARY OF THE INVENTION

By the present invention, it has now been found possible to prepare storage stable, pumpable, aqueous dispersions of aromatic diacyl peroxide compositions for use in curing polyester resins and the suspension polymerization of vinyl monomers.

The aqueous dispersions of the present invention contain an aromatic diacyl peroxide, a water-soluble alkylene glycol diluent, magnesium aluminum silicate, a cellulose ether compound and water. Being liquid, these compositions can be readily poured, pumped or sprayed into the system containing the unsaturated polyester resin or vinyl monomer. It has been found that these compositions are storage stable, thereby permitting their preparation at convenient intervals prior to their use. In addition, other additives such as, for example, emulsifiers, dispersants and stabilizers can be added to enhance various properties such as the viscosity and long term physical and chemical stability.

DETAILED DESCRIPTION

The amount of each component in the dispersion of the invention can be varied within suitable limits depending on the unsaturated polyester resin and monomer being reacted, the conditions of storage and other factors. A suitable water-soluble organic diluent is an alkylene glycol. Thus, the magnesium aluminum silicate and a cellulose ether compound need be present in a dispersion stabilizing amount. The concentration of aromatic diacyl peroxide can be varied depending on the utility. In general, however, it has been found that the following amounts of these components are useful:

| COMPONENT | WEIGHT % |
| --- | --- |
| Aromatic Diacyl Peroxide | 10–45 |
| Alkylene Glycol | 10–30 |
| Magnesium Aluminum Silicate | 0.5–3.0 |
| Cellulose Ether | 0.5–3.0 |
| Water | Remainder (Up to 100%) |

The symmetrical or asymmetrical aromatic diacyl peroxides useful in this invention have the following structure:

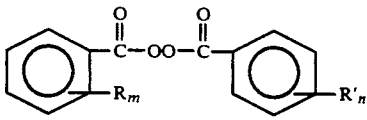

wherein R and R' are independently selected from the group consisting of methyl, ethyl, methoxy, ethoxy and halogen and m and n are integers from 0–3.

Among the symmetrical or asymmetrical aromatic diacyl peroxides that can be used in the compositions of this invention are benzoyl peroxide, bis o-toluoyl peroxide, bis(2,4-dichlorobenzoyl) peroxide, benzoyl o-toluoyl peroxide, benzoyl 2,4-dichlorobenzoyl peroxide, and o-toluoyl 2,4-dichlorobenzoyl peroxide and mixtures thereof. Due to its availability and performance characteristics, benzoyl peroxide is a preferred polymerization initiator. It is conveniently added as a 70% wetted material, although it may be added as pure dry granules. Preferably, it is present in a quantity of from about 30 to about 40 weight percent of the dispersion.

The magnesium aluminum silicate and cellulose ether are present in the dispersion in dispersion stabilizing amounts. Thus, the magnesium aluminum silicate can be present in an amount of about 0.5 to 3.0 weight percent of the dispersion, preferably in an amount of from about 0.70 to 2.8 weight percent of the dispersion.

The cellulose ether compound can be present in an amount of from about 0.5 to 3.0 weight percent of the dispersion, preferably in an amount from about 0.65 to 1.7 weight percent of the dispersion. Various cellulose ether compounds such as hydroxypropyl cellulose, hydroxypropyl methyl cellulose and hydroxyethyl cellulose can be used in the dispersion.

In addition, an organic diluent that has water solubility is a component of the present dispersion. In accordance with the storage stability feature of the present invention, preferred organic diluents are those which are relatively non-volatile. Water-soluble alkylene glycols have the proper properties for this component. Ethylene and propylene glycol are two of the preferred alkylene glycols, although other organic diluents with water-solubility can be used. The amount of organic diluent in the present dispersions will vary with the precise identity of the other components.

Sufficient water is required to form an aqueous dispersion. Thus, the water constitutes the remainder of the content of the dispersion.

The aqueous dispersions of this invention can be prepared by standard procedures for the preparation of dispersions. Briefly, the magnesium aluminum silicate is added to heated water with stirring. Then the cellulose ether compound is added slowly until there is obtained a uniform dispersion. Then the mixture is cooled to room temperature with continuous stirring. This is followed by the addition of the organic diluent. After this addition, the aromatic diacyl peroxide is added slowly to the mixture which is then stirred for about 30 minutes and passed through a homogenizer or other suitable mixing devices.

Other procedures known to those skilled in this art can be used for preparing the dispersions of this invention.

In order to demonstrate the storage stability of the aqueous dispersions of this invention, the following experiments were performed. Procedure A reports the method used in the preparation of Example 8 in Table I.

Tables I–III contain the details and results of 17 examples.

PROCEDURE A

Water (90 grams) was placed into a beaker on a hot plate and heated with stirring to 60° C. Then magnesium aluminum silicate (3 grams) was added slowly with vigorous stirring. After ten minutes of stirring, hydroxypropyl methyl cellulose (3 grams) was added slowly. Stirring was continued and when a uniform dispersion was obtained the mixture was cooled to room temperature. Ethylene glycol (90 grams) was added to the mixture followed by the addition of 70% by weight benzoyl peroxide (248 grams). Then the mixture was stirred for 30 minutes and passed through a hand operated homogenizer.

The viscosity was measured as 3,000 cps; the benzoyl peroxide content was determined by active oxygen analysis at about 40%; and the time for separation of the dispersion was determined at 40° C. and ambient temperature.

TABLE I

Storage Stability of Benzoyl Peroxide (BPO) Dispersions Containing Hydroxy Propyl Methyl Cellulose (HPMC) and Magnesium Aluminum Silicate (Mg Al Silicate)

| Example | H$_2$O | Mg Al Silicate[1] | HPMC[2] | EG[3] | BPO | Initial Viscosity (CPS) | Time for Separation of Dispersion Ambient | 40° C. |
|---|---|---|---|---|---|---|---|---|
| 1 | 54.10 | 2.10 | 0.65 | 25.40 | 17.75 | 100 | 16 Days | — |
| 2 | 53.80 | 2.10 | 1.25 | 25.20 | 17.65 | 500 | 69 Days | 46 Days |
| 3 | 71.90 | 2.80 | 1.70 | — | 23.60 | 8,000 | — | — |
| 4 | 50.50 | 1.80 | 1.10 | 21.65 | 24.95 | 2,600 | >3 Months | — |
| 5 | 50.85 | 1.10 | 1.10 | 21.80 | 25.15 | 1,300 | >3 Months | — |
| 6 | 51.15 | 1.10 | 0.55 | 21.95 | 25.25 | 300 | 1 Month | — |
| 7 | 37.45 | 1.65 | 1.00 | 20.05 | 39.85 | 5,000 | >3½ Months | — |
| 8 | 38.00 | 0.70 | 0.70 | 20.70 | 39.90 | 3,000 | 50 Days | 14 Days |

[1] Magnabrite HV from American Colloid Co.
[2] Methocel E50LV from Dow Chemical Co.
[3] Ethylene glycol

TABLE II

Storage Stability of Benzoyl Peroxide (BPO) Dispersions Containing Hydroxy Propyl Cellulose (HPC) or Hydroxy Ethyl Cellulose (HEC) and Magnesium Aluminum Silicate (Mg Al Silicate)

| Example | H$_2$O | Mg Al Silicate[1] | Cellulose Ether | EG[2] | BPO | Initial Viscosity (CPS) | Time for Separation of Dispersion Ambient | 40° C. |
|---|---|---|---|---|---|---|---|---|
| 9 | 54.25 | 1.25 | 1.25 HPC[3] | 25.45 | 17.80 | 175 | 3 Months | 27 Days |
| 10 | 53.30 | 2.10 | 2.10 HPC | 25.00 | 17.50 | 800 | 3.5 Months | 3.5 Months |
| 11 | 54.10 | 2.10 | 0.65 HEC[4] | 25.40 | 17.75 | 1,000 | 2 Months | — |
| 12 | 54.55 | 1.30 | 0.65 HEC | 25.60 | 17.90 | 800 | 8 Months | — |
| 13 | 53.80 | 2.10 | 1.25 HEC | 25.20 | 17.65 | 2,600 | 3.5 Months | 1 Month |

[1] Magnabrite HV from American Colloid Co.
[2] Ethylene glycol
[3] Klucel LF from Hercules, Inc.
[4] Natrosol 250 LR from Hercules, Inc.

TABLE III

Storage Stability of Dispersions Containing Other Aromatic Diacyl Peroxides

| Example | H$_2$O | Mg Al Silicate[1] | HPMC[2] | EG[3] | Peroxide | Initial Viscosity (CPS) | Time of Separation of Dispersion at Ambient Temperature |
|---|---|---|---|---|---|---|---|
| 14 | 53.35 | 2.10 | 1.25 | 25.20 | 18.10[4] | 1,400 | 1.5 Months |
| 15 | 58.80 | 1.30 | 0.85 | 25.50 | 13.55[5] | 700 | 4 Months |
| 16 | 53.80 | 2.10 | 1.25 | 25.20 | 17.65[6] | 300 | 1 Month |
| 17 | 55.50 | 1.25 | 1.25 | 25.45 | 16.55[7] | — | 7 Months |

[1] Magnabrite HV from American Colloid Co.
[2] Methocel E50LV from Dow Chemical Co.
[3] Ethylene glycol
[4] Bis-o-toluoyl peroxide
[5] Bis (2,4-dichlorobenzoyl) peroxide
[6] Mixture of benzoyl peroxide, benzoyl (2,4-dichloro benzoyl peroxide, and bis (2,4-dichlorobenzoyl peroxide)
[7] Mixture of benzoyl peroxide, benzoyl o-toluoyl peroxide, and bis o-toluoyl peroxide The use of the dispersions of this invention can be demonstrated by the curing of unsaturated polyester resin solutions.

The unsaturated polyester resin is a mixture of (i) an unsaturated polymer prepared by condensing an unsaturated acid component, a polyhydric alcohol, and optionally a saturated acid component, and (ii) a vinyl monomer that is copolymerizable with said unsaturated polyester. Unsaturated dicarboxylic acids used in preparing such an unsaturated polyester resin include maleic acid, fumaric acid, itaconic acid, citraconic acid and anhydrides thereof, such as maleic anhydride and itaconic anhydride. Saturated dicarboxylic acids include aliphatic dicarboxylic acids such as adipic acid, sebacic acid and succinic acids, aromatic dicarboxylic acids such as phthalic acid, isophthalic acid and terephthalic acid, anhydrides thereof such as succinic anhydride, and phthalic anhydride and halogenated derivatives of carboxylic acids or their anhydrides such as tetrachlorophthalic anhydride, tetrabromophthalic anhydride, HET acid and an adduct of the Diels-Alder reaction of hexachlorocyclopentadiene with tetrahydrophthalic anhydride.

Polyhydric alcohols include ethylene glycol, propylene glycol, diethylene glycol, dipropylene glycol, trimethylene glycol, butanediol-1,3, butanediol-1,4, hexanediol-1,6, neopentyl glycol, hydrogenated bisphenol A, a propylene oxide adduct of bisphenol A, an ethylene oxide adduct of bisphenol A, glycerin and pentaerythritol. Further, a condensation product of decachlorobiphenyl and monoethanol amine can also be used as a halogen-containing polyhydric alcohol.

Copolymerizable vinyl monomers include styrene, vinyl toluene, a-methyl styrene, chlorostyrene, t-butyl styrene, methyl methacrylate, ethyl methacrylate, vinyl acetate, diallyl phthalate and triallyl cryanurate.

Typically, the unsaturated polyester resin is primarily combined with a promoter. Promoted unsaturated polyester resins, particularly aryl-amine promoted unsaturated polyester resins, are generally contemplated for use in the present invention. Tertiary amines are particularly effective promoters for aromatic diacyl peroxides.

The determination of the amount of dispersion necessary to cure the unsaturated polyester resin necessarily depends on the content of the aromatic diacyl peroxide in the dispersion. Normally the use of aromatic diacyl peroxide in an amount between about 0.5 to about 5 weight percent of the unsaturated polyester resin will suffice, although it is preferred that the amount be between about 1 to about 2 weight percent of the resin.

Thus, the amount of dispersion to be used can be between about 1 and 50 weight percent of the unsaturated polyester resin; and preferably between about 2 and 33 weight percent of the resin.

In order to demonstrate the usefulness of the dispersions of this invention in the curing of polyester resins, the following experiments, Examples 18-24, were performed. Procedure B contains the general method used in the experiments and Table IV contain the details and results of the experiments.

bles I-III. Each dispersion was tested as a catalyst for curing an unsaturated polyester resin (Interplastic 135-279). A standard (Example 24) was also performed using a 50% active paste form of benzoyl peroxide.

A master batch was prepared by adding dimethylaniline (0.2 wt. %) to the resin and mixing thoroughly. A portion of the master batch (50.0 grams) is placed into a 3 oz. cup. The aromatic diacyl peroxide dispersion is added in an amount calculated to contain 0.5 grams of aromatic diacyl peroxide and mixed by hand for one minute. Then a temperature probe is placed in the middle of the cup and a spatula is used to "pick" the surface of the resin. When the resin gels, the time and temperature are recorded. As the resin begins to cure, the temperature is recorded every 15 seconds to determine the peak exotherm time and temperature.

All of the dispersions dissolved in the unsaturated polyester resin more easily than the standard. The cured castings became clearer and less milky as the amount of benzoyl peroxide (BPO) in the dispersion increased. The casting of Example 20 gave a clear casting in comparison to the standard.

While in the foregoing specification certain embodiments and examples of this invention have been described in detail, it will be apparent that modifications and variations therefrom will be apparent to those skilled in this art and that this invention is to be limited only by the scope of the appended claims.

I claim:

1. A method for stabilizing pumpable, aqueous dispersions of symmetrical or asymmetrical aromatic diacyl peroxide polymerization initiators comprising the steps of:
   (a) forming a suspension that contains from about 10% to about 45% by weight of a symmetrical or asymmetrical aromatic diacyl peroxide polymerization initiator in an aqueous medium that includes from about 10% to about 30% by weight of a water-soluble alkylene glycol diluent, from about 0.5% to about 3.0% by weight of a first suspending agent which is a magnesium aluminum silicate suspending agent and from about 0.5% to about 3.0% by weight of a second suspending agent selected from the group consisting of water-soluble cellulose ether suspending agents and mixtures thereof, said percentages being based on the weight of the suspension, and
   (b) mixing said suspension to form a stable, pumpable dispersion whereby the concentration of initiator is substantially uniform throughout said dispersion.

TABLE IV

| | | | Room Temperature Gel Tests | | | |
|---|---|---|---|---|---|---|
| Example | BPO (Wt %) | Corresponds to | Gel Time (Min & Sec) | Gel Temperature °F. | Exotherm Time (Min & Sec) | Peak Temperature °F. |
| 18 | 26.88 | Example 5, Table I | 13' 10" | 81 | 17' 30" | 414 |
| 19 | 31.17 | Table I | 13' 30" | 80 | 18' 0" | 408 |
| 20 | 42.77 | Example 8, Table I | 13' 35" | 81 | 18' 15" | 416 |
| 21 | 18.00 | Example 10, Table II | 13' 15" | 81 | 18' 0" | 389 |
| 22 | 19.78 | Example 11, Table II | 12' 45" | 81 | 16' 45" | 401 |
| 23 | 20.65[1] | Example 14, Table III | 6' 45" | 80 | 10' 30" | 389 |
| 24 | 51.53 | Standard[2] | 12' 40" | 82 | 17' 45" | 412 |

[1] Bis-o-toluoyl peroxide
[2] BZQ ®-50

PROCEDURE B

Examples 18-23 were performed with six aqueous peroxide dispersions similar to those contained in Tables I-III.

2. The method of claim 1 wherein the water-soluble alkylene glycol is ethylene glycol.

3. The method of claim 1 wherein the water-soluble alkylene glycol is propylene glycol.

4. The method of claim 1, wherein the symmetrical or asymmetrical aromatic diacyl peroxide is benzoyl peroxide, bis-o-toluoyl peroxide, bis 2,4-dichlorobenzoyl peroxide, benzoyl o-toluoyl peroxide, benzoyl 2,4-dichlorobenzoyl peroxide or o-toluoyl 2,4-dichlorobenzoyl peroxide and mixtures thereof.

5. The method of claim 1 wherein the symmetrical or asymmetrical aromatic diacyl peroxide is benzoyl peroxide.

6. The method of claim 1 wherein the symmetrical or asymmetrical aromatic diacyl peroxide is present in an amount from about 30 to about 40 weight percent of the dispersion.

7. The method of claim 1 wherein said first suspending agent is present in an amount of from about 0.7 to about 2.8 weight percent of the dispersion.

8. The method of claim 1 wherein said second suspending agent is selected from the group consisting of hydroxypropyl cellulose, hydroxypropyl methyl cellulose and hydroxyethyl cellulose and mixtures thereof.

9. The method of claim 1 wherein said mixing step includes homogenizing said suspension.

* * * * *